United States Patent [19]

Seele et al.

[11] Patent Number: 5,077,303

[45] Date of Patent: Dec. 31, 1991

[54] OXIRANE PHENYL ESTERS AND FUNGICIDES CONTAINING THESE

[75] Inventors: Rainer Seele, Fussgoenheim; Franz Schuetz, Ludwigshafen; Horst Wingert; Hubert Sauter, both of Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 497,605

[22] Filed: Mar. 22, 1990

[30] Foreign Application Priority Data

Apr. 11, 1989 [DE] Fed. Rep. of Germany ....... 3911724
May 23, 1989 [DE] Fed. Rep. of Germany ....... 3916719

[51] Int. Cl.$^5$ ..................... A61K 31/44; C07D 405/04
[52] U.S. Cl. ..................................... 514/336; 514/374; 514/378; 514/444; 514/449; 514/471; 514/475; 546/268; 548/215; 548/240; 549/60; 549/472; 549/551; 549/561
[58] Field of Search ................ 549/551, 561, 60, 472; 514/449, 475, 336, 374, 378, 444, 471; 546/268; 548/215, 240

[56] References Cited

U.S. PATENT DOCUMENTS

| | | | |
|---|---|---|---|
| 3,459,775 | 8/1969 | Rick et al. | 549/561 |
| 4,018,801 | 4/1977 | Ozretich | 549/551 |
| 4,672,134 | 6/1987 | Holmwood et al. | 549/551 |
| 4,782,177 | 11/1988 | Schirmer et al. | 560/60 |
| 4,785,004 | 11/1988 | Von Sprecher et al. | 514/311 |

FOREIGN PATENT DOCUMENTS

| | | | |
|---|---|---|---|
| 254086 | 1/1988 | European Pat. Off. | 549/561 |
| 3519282 | 5/1985 | Fed. Rep. of Germany. | |

*Primary Examiner*—C. Warren Ivy
*Assistant Examiner*—Ba K. Trinh
*Attorney, Agent, or Firm*—Oblon, Spivak, McClelland, Maier & Neustadt

[57] ABSTRACT

Esters of the general formula I

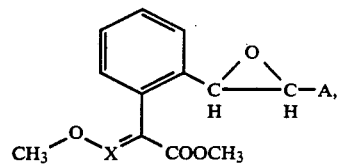

where A is hydrogen, alkyl, cycloalkyl, cycloalkenyl, naphthyl, biphenyl, hetaryl or phenyl, these radicals being substituted or unsubstituted, and X is CH or N, and fungicides containing these esters.

9 Claims, No Drawings

OXIRANE PHENYL ESTERS AND FUNGICIDES CONTAINING THESE

The present invention relates to novel esters which contain an oxirane residue and a phenyl radical, to fungicides containing these and to the use thereof as fungicides.

It is known to use N-tridecyl-2,6-dimethylmorpholine (DE 1 164 152) or methyl α-phenyl-β-methoxyacrylate derivatives (DE 3 519 282.8) as fungicides. However, in some cases their action is inadequate.

We have now found that novel esters of the formula I

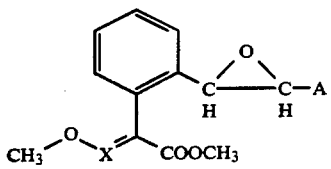

where A is hydrogen, $C_1$-$C_6$-alkyl, $C_3$-$C_6$-cycloalkyl, $C_5$-$C_6$-cycloalkenyl, naphthyl, biphenylyl, hetaryl or phenyl, it being possible for these radicals to be substituted one to three times by halogen, nitro, phenoxy, amino, alkyl, alkoxy or haloalkyl having 1 to 4 C atoms in each case, and X is N or CH, have a better fungicidal action than known acrylic esters.

The novel compounds of the formula I may result from the preparation as mixtures of stereoisomers (E/Z-isomers, diastereomers, enantiomers) which can be separated in a conventional manner, e.g. by crystallization or chromatography, into the individual components. Both the individual isomers and mixtures thereof can be used as fungicides, and the invention relates to all of them.

Examples of A are $C_1$-$C_6$-alkyl, ($C_1$-$C_4$-alkyl), methyl, ethyl, propyl, butyl or $C_3$-$C_6$-cycloalkyl, cyclopropyl, cyclohexyl or $C_5$-$C_6$-cycloalkenyl, cyclohexenyl, hetaryl, pyridyl, furyl, thienyl, oxazolyl or isoxazolyl. Examples of substituents are halogen (F, Cl, Br, I), $C_1$-$C_4$-alkyl (methyl, ethyl, propyl, butyl), $C_1$-$C_4$-alkoxy (methoxy, ethoxy, propoxy) or haloalkyl (trifluoromethyl). Examples of A are chlorophenyl, fluorophenyl, bromophenyl, methoxyphenyl, phenoxyphenyl or tert-butylphenyl.

The compounds of the formula I can be prepared, for example, by converting a compound of the formula III

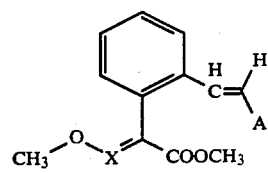

where A and X have the abovementioned meanings, into the epoxide. This entails oxidation of the olefins III with peroxycarboxylic acids such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid in inert solvents, preferably chlorohydrocarbons, e.g. methylene chloride, chloroform, tetrachloromethane, dichloroethane or in acetic acid, ethyl acetate, acetone or dimethylformamide, in the presence or absence of a buffer such as sodium acetate, sodium carbonate or disodium hydrogen phosphate. The reaction is carried out at from 10° to 100° C. and can be catalyzed with, for example, iodine, sodium tungstate or light. Also suitable for oxidation are alkaline solutions of hydrogen peroxide (about 30% strength) in methanol, ethanol, acetone or acetonitrile at from 25° to 30° C., and alkyl hydroperoxides, e.g. tert-butyl hydroperoxide, with the addition of a catalyst, e.g. sodium tungstate, pertungstic acid, molybdenum hexacarbonyl or vanadyl acetylacetonate. The said oxidizing agents can in some cases be generated in situ.

The compounds of the formula III can be prepared by conventional processes (cf. EP 178826, EP 203606 and EP 253213).

The compounds of the general formula I in which X is CH are also obtained from the substituted methyl α-aryl-β-hydroxyacrylate derivatives of the general formula VII, which may be in equilibrium with the formyl derivatives VIII, by reaction with an alkylating agent (e.g. dimethyl sulfate or methyl iodide) in the presence of a base (e.g. potassium carbonate or sodium carbonate) in a diluent (e.g. acetone). In the formulae depicted hereinafter, "L" is a leaving group (e.g. methosulfate or iodide).

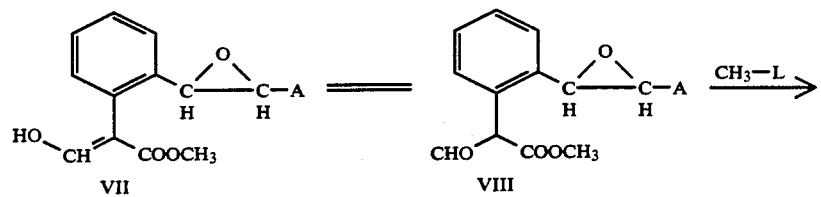

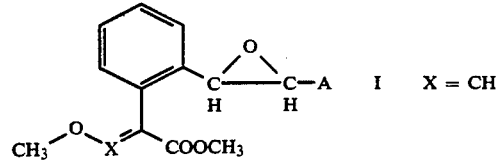

The methyl α-aryl-β-hydroxyacrylates of the general formula VII are obtained from the substituted methyl phenylacetates of the general formula II by reaction with methyl formate in the presence of a base (e.g. sodium hydride, lithium diisopropylamide or sodium methanolate) in an inert solvent such as diethyl ether or tetrahydrofuran (cf. Ann. Chem. 424 (1921) 214).

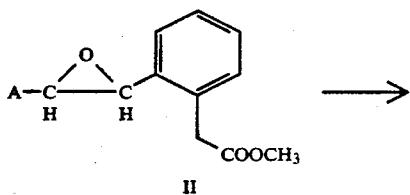

II

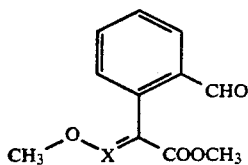

VII

The compounds of the formula I in which A is hydrogen can be prepared by reacting a compound of the formula IV

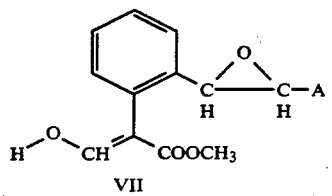

IV in which X is CH, with a sulfur ylide of the formula V

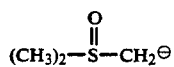

V (cf. Corey, Chaykovsky, J. A. C. S. 84 (1962) 3782).

The compounds of the formula IV can be prepared by conventional methods (cf. EP 278595).

Compounds of the formula I in which A is hydrogen and X is N can be prepared in a corresponding manner by using a compound of the formula IV in which X is N as starting material.

The compound of the formula IV in which X is N can be prepared as follows: Methyl 2-formylphenylglyoxylate O-methyloxime 20 g (0.07 mol) of methyl 2-bromomethylphenylglyoxyl O-methyloxime are dissolved in 300 ml of CCl₄. 32 g (0.237 mol) of methylmorpholine N-oxide monohydrate are added, and the mixture is refluxed for 9 hours. The solid is filtered off. The CCl₄ phase is washed with water, with 2N HCl and again with water, dried and concentrated. The residue is recrystallized from pentane. 9.0 g of the product (58%) are obtained as colorless crystals. M.p. 100°-105° C.; IR (cm⁻¹): 1725, 1690, 1443, 1214, 1204, 1074, 1042, 1020, 951, 756.

The styrene oxides of the formula I in which A is hydrogen and X is CH or N

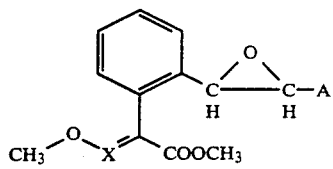

I are suitable as fungicides and, moreover, are intermediates for the synthesis of novel ester derivatives.

These styrene oxides are particularly suitable for the preparation of other fungicidal compounds by reaction with various nucleophiles, e.g. with phenol.

The compounds of the formula II can be prepared by converting a compound of the formula VI

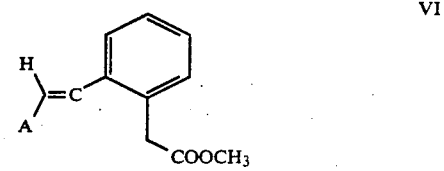

VI in which A has the abovementioned meaning, into the corresponding epoxide. This entails oxidation of the olefins VI with peroxycarboxylic acids such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid in inert solvents, preferably chlorohydrocarbons, e.g. methylene chloride, chloroform, tetrachloromethane, dichloroethane or in acetic acid, ethyl acetate, acetone or dimethylformamide, in the presence or absence of a buffer such as sodium acetate, sodium carbonate or disodium hydrogen phosphate. The reaction is carried out at from 10° to 100° C. and can be catalyzed with, for example, iodine, sodium tungstate or light. Also suitable for the oxidation are alkaline solutions of hydrogen peroxide (about 30% strength) in methanol, ethanol, acetone or acetonitrile at from 25° to 30° C., and alkyl hydroperoxides, e.g. tert-butyl hydroperoxide, with the addition of a catalyst, e.g. sodium tungstate, pertungstic acid, molybdenum hexacarbonyl or vanadyl acetylacetonate. The said oxidizing agents can in some cases be generated in situ.

The substituted methyl phenylacetates VI required as starting compounds are prepared by reacting a methyl 2-formylphenylacetate IX with a methanephosphonic ester of the general formula X (A has the abovementioned meaning, R¹=methyl or ethyl). The reaction is carried out in a conventional manner (cf. e.g. J. Am. Chem. Soc. 83 (1961) 1733). The starting materials are normally employed in the stoichiometric ratio. It is possible to have an excess of up to 10% (% by weight) of one of the two reactants. The reaction is expediently carried out in an inert solvent or diluent (e.g. diethyl ether, tetrahydrofuran, methyl tert-butyl ether, dimethoxyethane, toluene, dimethyl sulfoxide) in the presence of an equivalent amount of a base (e.g. sodium hydride, sodium amide, potassium tert-butylate, sodium methanolate, butyllithium, phenyllithium, sodium bis-trimethylsilylamide, sodium methylsulfinylmethyl). The reactions usually take place at from −70° C. to 30° C. Since they take place with evolution of heat in some cases, it may be advantageous to provide means of cooling.

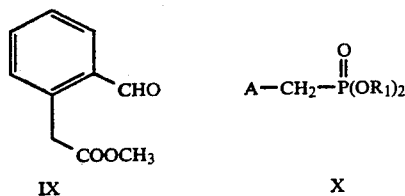

Methyl 2-formylphenylacetate IX is obtained by esterification of 2-formylphenylacetic acid XI with methanol under standard conditions. 2-Formylphenylacetic acid XI is prepared in a straightforward manner by ozonolysis of the trimethylsilyl enol ether XIII of 2-indanone XII (Tetrahedron Lett. 25 (1984) 3659; Tetrahedron 43 (1987) 2075).

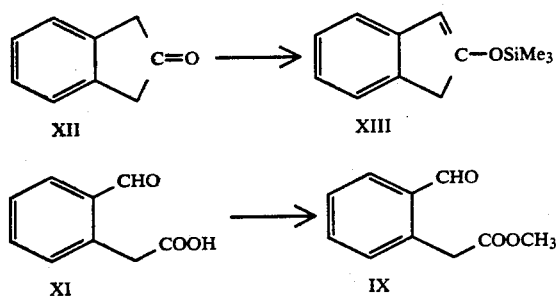

The substituted methanephosphonic esters of the general formula X (A has the abovementioned meaning, $R^1$=methyl or ethyl) are obtained by reacting appropriate methyl halides with trimethyl or triethyl phosphite $P(OR^1)_3$ (cf. Methoden der organischen Chemie, Volume 12/1, p. 433, Thieme, Stuttgart 1963).

The examples and procedures which follow explain the preparation of the active compounds and their precursors.

PROCEDURE 1

Methyl 2-(2-phenylethenyl)phenylacetate

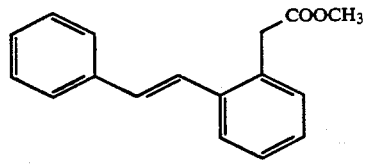

7.0 g (0.057 mol) of potassium tert-butylate are added to a suspension of 24.0 g (0.062 mol) of benzyltriphenylphosphonium chloride in 300 ml of diethyl ether at room temperature (20° C.). The mixture is then stirred at room temperature for 30 minutes and cooled to 10° C., and then 10.0 g (0.056 mol) of 2-formylphenylacetic acid in 20 ml of diethyl ether are added. The reaction mixture is stirred at room temperature for 12 hours. It is hydrolyzed with 300 ml of water and extracted with diethyl ether, and the solvent is removed in a rotary evaporator. The residue is taken up in n-hexane, and the precipitated triphenylphosphine oxide is removed. The filtrate is concentrated and chromatographed on silica gel (9:1 cyclohexane/ethyl acetate). 11.8 g (83%) of methyl 2-(2-phenylethenyl)phenylacetate (E/Z=3:1) are obtained as a colorless oil.

PROCEDURE 2

Methyl 2-(3-phenyl-2-oxiranyl)phenylacetate

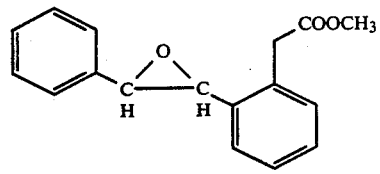

7.8 g of m-chloroperbenzoic acid (about 50% pure) are added to a solution of 6 g of methyl 2-(2-phenylethenyl)phenylacetate (E/Z=3:1) in 50 ml of methylene chloride. The reaction mixture is refluxed for 12 hours and then the precipitate is filtered off with suction and the filtrate is washed twice with saturated sodium bicarbonate solution and water. The isolated organic phase is dried over sodium sulfate and concentrated, and the residue is recrystallized from methyl tert-butyl ether. 3.1 g (48%) of methyl trans-2-(3-phenyl-2-oxiranyl)phenylacetate are obtained of melting point 118°–119° C. Chromatography of the mother liquor on silica gel (6:1 ethyl acetate/n-hexane) yields 2.8 g (44%) of methyl 2-(3-phenyl-2-oxiranyl)phenylacetate as a 1:1 cis/trans mixture.

EXAMPLE 1

Methyl 2-[2-(3-phenyl-2-oxiranyl)phenyl]-3-methoxyacrylate (compound No. 1a)

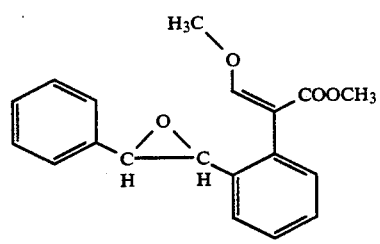

7.2 g of m-chloroperbenzoic acid (about 50% pure) are added to a solution of 10.2 g of methyl 2-[2-(2-phenylethenyl)phenyl]-3-methoxyacrylate in 80 ml of methylene chloride. The reaction mixture is refluxed for two days and then the precipitate is filtered off with suction and the filtrate is washed twice with saturated sodium bicarbonate solution and water. The isolated organic phase is dried over sodium sulfate and concentrated, and the residue is recrystallized from methyl tert-butyl ether. 6.2 g (58%) of methyl trans-2-[2-(3-phenyl-2-oxiranyl)phenyl]-3-methoxyacrylate are obtained of melting point 110°–113° C.

The intermediates listed in Table 1 can be prepared by procedure 2.

The compounds listed in Table 2 can be prepared as in Example 1.

TABLE 1

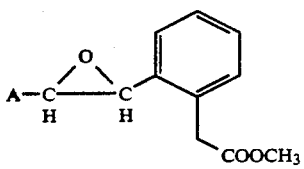

| Ex. | A | m.p./IR | Isomer* |
|---|---|---|---|
| 1 | C₆H₅ | 118-119° C. | trans |
| 2 | C₆H₅ | | cis/trans = 1:1 |
| 3 | 4-Cl—C₆H₄ | | |
| 4 | 3-Cl—C₆H₄ | | |
| 5 | 2-Cl—C₆H₄ | | |
| 6 | 2,4-Cl₂—C₆H₃ | | |
| 7 | 3,4-Cl₂—C₆H₃ | | |
| 8 | 2-Cl-4-F—C₆H₃ | | |
| 9 | 2-F—C₆H₄ | | |
| 10 | 4-F—C₆H₄ | | |
| 11 | 2,4-F₂—C₆H₃ | | |
| 12 | 2-Br—C₆H₄ | | |
| 13 | 4-Br—C₆H₄ | | |
| 14 | 4-NO₂—C₆H₄ | | |
| 15 | 4-NH₂—C₆H₄ | | |
| 16 | 2-OCH₃—C₆H₄ | | |
| 17 | 4-OCH₃—C₆H₄ | | |
| 18 | 4-OC₆H₅—C₆H₄ | | |
| 19 | 2-CH₃—C₆H₄ | | |
| 20 | 4-tert.-C₄H₉—C₆H₄ | | |
| 21 | 2-CF₃—C₆H₄ | | |
| 22 | 3-CF₃—C₆H₄ | | |
| 23 | 4-CF₃—C₆H₄ | | |
| 24 | 4-C₆H₅—C₆H₄ | | |
| 25 | 1-naphthyl | | |
| 26 | 2-naphthyl | | |
| 27 | H | | |
| 28 | CH₃ | | |
| 29 | C₂H₅ | | |
| 30 | C₃H₇ | | |
| 31 | iso-C₃H₇ | | |
| 32 | C₆H₁₂ | | |
| 33 | cyclopropyl | | |
| 34 | cyclopentyl | | |
| 35 | cyclohexyl | | |
| 36 | 2-cyclohexenyl | | |
| 37 | 3-cyclohexenyl | | |
| 38 | 3-pyridyl | | |
| 39 | 2-furyl | | |
| 40 | 2-thienyl | | |
| 41 | 3-thienyl | | |
| 42 | 1,3-oxazol-5-yl | | |

*"cis/trans" refers to the configuration on the oxirane ring

TABLE 2

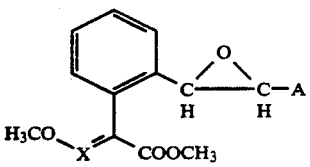

| Ex. | A | X | m.p./IR | Isomer* |
|---|---|---|---|---|
| 1a | C₆H₅ | CH | 110-113° C. | trans |
| 2a | C₆H₅ | CH | | cis |
| 3a | C₆H₅ | N | | |
| 4a | 4-Cl—C₆H₄ | CH | | |
| 5a | 4-Cl—C₆H₄ | N | | |
| 6a | 3-Cl—C₆H₄ | CH | | |
| 7a | 2-Cl—C₆H₄ | N | | |
| 8a | 3-Cl—C₆H₄ | N | | |
| 9a | 2-Cl—C₆H₄ | CH | | |
| 10a | 2,4-Cl₂—C₆H₃ | CH | 90° C. | trans |
| 11a | 2,4-Cl₂—C₆H₃ | N | | |
| 12a | 3,4-Cl₂—C₆H₃ | CH | | |
| 13a | 3,4-Cl₂—C₆H₃ | N | | |
| 14a | 2-F—C₆H₄ | CH | | |
| 15a | 2-F—C₆H₄ | N | | |
| 16a | 4-F—C₆H₄ | CH | | |
| 17a | 4-F—C₆H₄ | N | | |
| 18a | 2,4-F₂—C₆H₃ | CH | | |
| 19a | 2,4-F₂—C₆H₃ | N | | |
| 20a | 2-Br—C₆H₄ | CH | | |
| 21a | 2-Br—C₆H₄ | N | | |
| 22a | 4-Br—C₆H₄ | CH | | |
| 23a | 4-Br—C₆H₄ | N | | |
| 24a | 4-NO₂—C₆H₄ | CH | | |
| 25a | 4-NO₂—C₆H₄ | N | | |
| 26a | 4-NH₂—C₆H₄ | CH | | |
| 27a | 4-NH₂—C₆H₄ | N | | |
| 28a | 2-OCH₃—C₆H₄ | CH | | |
| 29a | 2-OCH₃—C₆H₄ | N | | |
| 30a | 4-OCH₃—C₆H₄ | CH | | |
| 31a | 4-OCH₃—C₆H₄ | N | | |
| 32a | 4-C₆H₅O—C₆H₄ | CH | | |
| 33a | 4-C₆H₅O—C₆H₄ | N | | |
| 34a | 2-CH₃—C₆H₄ | CH | | |
| 35a | 2-CH₃—C₆H₄ | N | | |
| 36a | 4-tert.-C₄H₉—C₆H₄ | CH | | |
| 37a | 4-tert.-C₄H₉—C₆H₄ | N | | |
| 38a | 2-CF₃—C₆H₄ | CH | | |
| 39a | 2-CF₃—C₆H₄ | N | | |
| 40a | 3-CF₃—C₆H₄ | CH | | |
| 41a | 3-CF₃—C₆H₄ | N | | |
| 42a | 4-CF₃—C₆H₄ | CH | | |
| 43a | 4-CF₃—C₆H₄ | N | | |
| 44a | 4-C₆H₅—C₆H₄ | CH | | |
| 45a | 4-C₆H₅—C₆H₄ | N | | |
| 46a | 3-C₆H₅—C₆H₄ | CH | 112° C. | trans |
| 47a | 3-C₆H₅—C₆H₄ | N | | |
| 48a | 1-naphthyl | CH | | |
| 49a | 1-naphthyl | N | | |
| 50a | 2-naphthyl | CH | | |
| 51a | 2-naphthyl | N | | |
| 52a | H | CH | | |
| 53a | H | N | 65-67° C. | |
| 54a | CH₃ | CH | | |
| 55a | CH₃ | N | | |
| 56a | C₂H₅ | CH | | |
| 57a | C₂H₅ | N | | |
| 58a | C₃H₇ | CH | | |
| 59a | C₃H₇ | N | | |
| 60a | iso-C₃H₇ | CH | | |
| 61a | iso-C₃H₇ | N | | |
| 62a | cyclopropyl | CH | | |
| 63a | cyclopropyl | N | | |
| 64a | cyclopentyl | CH | | |
| 65a | cyclopentyl | N | | |
| 66a | cyclohexyl | CH | | |
| 67a | cyclohexyl | N | | |
| 68a | 2-cyclohexenyl | CH | | |
| 69a | 3-cyclohexenyl | N | | |
| 70a | 2-cyclohexenyl | N | | |
| 71a | 3-cyclohexenyl | CH | | |
| 72a | 3-pyridyl | CH | | |
| 73a | 3-pyridyl | N | | |
| 73a | 3-pyridyl | N | | |
| 74a | 2-furyl | CH | | |
| 75a | 2-furyl | N | | |
| 76a | 2-thienyl | CH | | |
| 77a | 2-thienyl | N | | |
| 78a | 3-thienyl | CH | | |
| 79a | 3-thienyl | N | | |
| 89a | 1,3-oxazol-5-yl | CH | | |
| 81a | 1,3-oxazol-5-yl | N | | |

*"cis/trans" refers to the configuration on the oxirane ring

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1a (Table 2) is mixed with 10 parts by weight of N-methyl-α-pyrrolidone. A mixture is obtained which is suitable for application in the form of very fine drops.

II. 20 parts by weight of compound no. 1a is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1a is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1a is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1a is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1a is intimately mixed with 97 parts by weight of particulate kaolin. A dust is obtained containing 3% by weight of the active ingredient.

VII. 30 parts by weight of compound no. 1a is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1a is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 1a is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLES

For comparison purposes, the compound N-tridecyl-2,6-dimethylmorpholine (A) disclosed in DE 1,164,152 was used.

USE EXAMPLE

Action on *Pyricularia oryzae* (protective)

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in a climatic cabinet at 22°–24° C. and a relative humidity of 95–99%. The extent of fungus spread was determined after 6 days.

The results show that active ingredient 1a (Table 2), applied as a 0.05 wt. % spray liquor, had a better fungicidal action (95%) than prior art active ingredient A (65%).

We claim:

1. An ester of the formula I:

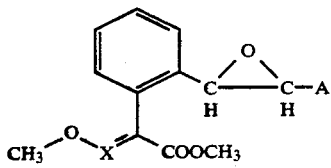

wherein A is hydrogen or unsubstituted $C_1$–$C_6$ alkyl, $C_3$–$C_6$ cycloalkyl, $C_5$–$C_6$-cycloalkenyl, naphthyl, biphenyl, phenyl, pyridyl, furyl, thienyl, oxazolyl or isooxazolyl, or said radicals being mono- to trisubstituted by halogen, nitro, phenoxy, amino, $C_1$–$C_4$ alkyl, $C_1$–$C_4$ alkoxy or $C_1$–$C_4$ haloalkyl, and X is CH or N.

2. The ester of claim 1, wherein A is phenyl which is unsubstituted or is substituted by one or two identical or different substituents selected from the group consisting of fluorine, chloride, bromine and trifluoromethyl.

3. The ester of claim 1, wherein A is phenyl, and X is CH.

4. A fungicidal composition containing:

a) a fungicidally effective amount of one or more esters of the formula I:

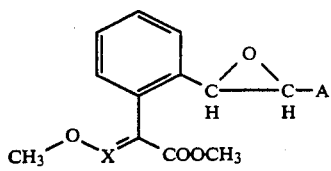

wherein A is hydrogen or unsubstituted $C_1$–$C_6$ alkyl, $C_3$–$C_6$ cycloalkyl, $C_5$–$C_6$-cycloalkenyl, naphthyl, biphenyl, phenyl, pyridyl, furyl, thienyl, oxazolyl or isooxazolyl, or said radicals being mono- to trisubstituted by halogen, nitro, phenoxy, amino, $C_1$–$C_4$ alkyl, $C_1$–$C_4$ alkoxy or $C_1$–$C_4$ haloalkyl, and X is CH or N; and b) a carrier.

5. The fungicidal composition of claim 4, wherein A represents phenyl which is unsubstituted or substituted by one or two identical or different substituents selected from the group consisting of fluorine, chlorine, bromine and trifluoromethyl.

6. The fungicidal composition of claim 1, wherein A is phenyl, and X is CH.

7. A process for combatting fungi, which comprises applying to fungi, or on materials, spaces, plants or seeds threatened by fungi attack, a fungicidally effective amount of an ester of the formula I:

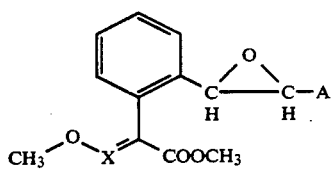

wherein A is hydrogen or unsubstituted $C_1$–$C_6$ alkyl, $C_3$–$C_6$ cycloalkyl, $C_5$–$C_6$-cycloalkenyl, naphthyl, biphenyl, phenyl, pyridyl, furyl, thienyl, oxazolyl or isooxazolyl, or said radicals being mono- to trisubstituted by halogen, nitro, phenoxy, amino, $C_1$–$C_4$ alkyl, $C_1$–$C_4$ alkoxy or $C_1$–$C_4$ haloalkyl, and X is CH or N.

8. The process of claim 7, wherein A represents phenyl which is unsubstituted or substituted by one or two identical or different substituents selected from the group consisting of fluorine, chlorine, bromine and trifluoromethyl.

9. The process of claim 7, wherein A is phenyl, and X is CH.

* * * * *